(12) United States Patent
Hsu et al.

(10) Patent No.: US 7,845,214 B2
(45) Date of Patent: Dec. 7, 2010

(54) DEVICE AND METHOD FOR OPTICAL NANOINDENTATION MEASUREMENT

(75) Inventors: Jiong-Shiun Hsu, Taichung (TW);
Hui-Ching Lu, Hsinchu (TW);
Chung-Lin Wu, Hsinchu (TW);
Sheng-Jui Chen, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 328 days.

(21) Appl. No.: 12/230,340

(22) Filed: Aug. 28, 2008

(65) Prior Publication Data
US 2009/0165537 A1   Jul. 2, 2009

(30) Foreign Application Priority Data
Dec. 26, 2007   (TW) .............................. 96150224 A

(51) Int. Cl.
*G01N 3/48* (2006.01)
(52) U.S. Cl. ............................................. 73/81
(58) Field of Classification Search ................. 73/81, 73/12.12
See application file for complete search history.

(56) References Cited

U.S. PATENT DOCUMENTS

| | | | |
|---|---|---|---|
| 2005/0103120 A1* | 5/2005 | Liu et al. | 73/821 |
| 2006/0186874 A1* | 8/2006 | Mackin et al. | 324/158.1 |
| 2007/0151340 A1* | 7/2007 | Hsu et al. | 73/573 |

* cited by examiner

*Primary Examiner*—Hezron Williams
*Assistant Examiner*—Tamiko D Bellamy
(74) *Attorney, Agent, or Firm*—Bacon & Thomas, PLLC

(57) ABSTRACT

This invention relates to a device and method for optical nanoindentation measurement, according to which respective measurement results are obtained by having an indenter tip apply load to a fixed portion of a thin film, having an indenter tip apply load to a non-fixed portion of a thin film, and having a vibrating component transmit the dynamic properties of the vibration to the thin film. By combining the above measurement results in calculations, the Young's modulus, the Poisson's ratio, and the density of the thin film can be obtained.

22 Claims, 3 Drawing Sheets

DEVICE AND METHOD FOR OPTICAL NANOINDENTATION MEASUREMENT

BACKGROUND OF THE INVENTION

1. Field of the Invention

The present invention relates to a device and method for measurement, especially a device and method for optical nanoindentation measurement.

2. Description of the Related Art

The wide application of thin film in the semiconductor, micro-mechanical, solar energy, and display industries over the past few years has made the mechanical properties of thin film an influencing element in deciding the performance and the service life of product. The thickness of thin film is so thin that it distinguishes itself from bulk materials in terms of mechanical properties, and so much so that traditional experimental design has been rendered inadequate to measure the mechanical properties of thin film. To tackle the problem, a variety of methods, such as bulge test, nanoindentation test, and micro tensile test, etc., have been developed in attempts to measure the mechanical properties of thin film. Nanoindentation test, in particular, has attracted strong audience in both academia and industry for its accessibility and straightforwardness. Current nanoindentation measurement systems used by academia and industry are all designed and made by international manufacturers, capable of measuring the reduced modulus and the hardness of thin film. However, the reduced modulus obtained represents only the relationship between the Young's modulus and the Poisson's ratio of the thin film, not the Young's modulus and the Poisson's ratio, respectively. Or, an estimate of Poisson's ratio has to be made before the Young's modulus can be obtained. Nevertheless, if the estimation of the Poisson's ratio is significantly different from the reality, the accuracy of the obtained Young's modulus will be compromised, too. In addition, traditional nanoindentation measurement systems are unable to measure the density, another important mechanical property, of the thin film as well.

FIG. 5 shows a schematic view of thin film 51 indentation process undertaken by traditional nanoindentation measurement system. In this figure, A-A' represents the indentation of the thin film 51 under the applied load F of the indenter tip; B-B' represents the residual indentation of the thin film 51 after the removal of the indenter tip; and C-C' represents the initial surface of the thin film 51. The relationship between the maximum indentation depth $h_{max}$, the contact depth $h_c$, and the distance between the contact position and the initial surface of the thin film 51, $h_s$, is defined as follows: $h_{max}=h_c+h_s$. Besides, according to Oliver and Pharr's findings, the unloading data illustrated in FIG. 6 can be represented by a power-law function: $P=K(h-h_f)^m$, where P is the applied load, $h_f$ is the residual depth, and K and m are constants fitted by the unloading experimental data. The contact stiffness S is defined as the slop of the unloading curve at the time the maximum load is applied, as FIG. 6 shows, and can be obtained through the formula $$S = \frac{dP}{dh}\bigg|_{h=h_{max}}.$$

Moreover, the area function A of the indentation tip of the thin film 51 can be obtained by applying the following formula:

$$A(h_c)=C_0 h_c^2+C_1 h_c^1+C_2 h_c^{1/2}+C_3 h_c^{1/4}+\ldots+C_8 h_c^{1/128},$$

where $C_0$ to $C_8$ are fitted constants. And, by applying the theory of contact mechanics, the following relation can be obtained:

$$h_s = \varepsilon \frac{P_{max}}{S},$$

where $\varepsilon$ represents a constant determined by the geometry of the indenter tip. Besides, because $P_{max}$ and S are known, $h_s$ can be obtained as well. In addition, based on the formula $h_{max}=h_c+h_s$, $h_c$ is obtained, and, therefore, the area function $A(h_c)$ is obtained.

Finally, by applying the contact stiffness S and the area function A of the indentation tip to the following formula, the reduced modulus $E_r$ of the thin film 51 can be obtained:

$$E_r = \frac{S}{2}\sqrt{\frac{\pi}{A}}$$

However, due to the fact that the relationship between $E_r$, the Young's modulus, and the Poisson's ratio is defined by $$\frac{1}{E_r} = \frac{1-v_1^2}{E_1} + \frac{1-v_2^2}{E_2},$$

traditional nanoindentation systems, as mentioned above, are only able to provide the relationship between the Young's modulus and the Poisson's ratio, not the respective values thereof. Therefore, to improve the accuracy of the Young's modulus of the thin film measured by traditional measurement systems and to enhance both the capacities and techniques of current nanoindentation measurement systems, a measuring technique combing nanoindentation and optical interference is developed, not only to improve the accuracy of the Young's modulus of the thin film measured by traditional nanoindentation measurement systems, but also to make possible the measurement of the Poisson's ratio and the density of the thin film otherwise unobtainable through traditional nanoindentation measurement systems. As a result, not only can nanoindentation test be made much more competitive in the market, but the mechanical properties of thin film can be better understood as well.

SUMMARY OF THE INVENTION

The present invention provides a device and method for optical nanoindentation measurement, according to which respective measurement results are obtained by having an indenter tip apply load to fixed portion of thin film, having an indenter tip apply load to non-fixed portion of a thin film, and having a vibrating component transmit the dynamic properties of the vibration to the thin film. By combining the above measurement results in calculations, the Young's modulus, the Poisson's ratio, and the density of the thin film can be obtained.

To achieve the objective, the device for optical nanoindentation measurement according to the present invention comprises: a measuring station; an indenter tip mounted on the measuring station, capable of moving along the measuring station; a vibrating component mounted on the measuring station for causing vibration; a thin film; and an optical transceiver for measuring the displacement of the thin film.

The present invention further comprises a function generator connected to the vibrating component for providing vibration signals with different frequencies to the vibrating component to have the vibrations generated by the vibrating component transmitted to the thin film.

To achieve the objective, the method for optical nanoindentation measurement according to the present invention comprises the steps of: having an indenter tip make indentation in a fixed portion of a thin film; having the indenter tip make indentation in a non-fixed portion of the thin film; having an optical transceiver measure the displacement of the thin film; having a vibrating component provide vibrations with different frequencies to the thin film and having the optical transceiver measure the resonant frequency of the thin film; and measuring the above indentation results so as to obtain Young's modulus, Poisson's ratio and density.

The non-fixed portion of the thin film is located at a predetermined distance from the fixed portion of the thin film.

The displacement of the thin film measured by the optical transceiver represents the deflection of the thin film caused by the indentation made by the indenter tip in the non-fixed portion of the thin film.

The present invention further comprises a function generator connected to the vibrating component for providing vibrations with different frequencies to the vibrating component.

In short, the present invention not only improves the accuracy of the Young's modulus of the thin film measured by traditional nanoindentation measurement systems, but also makes possible the measurement of the Poisson's ratio and the density of the thin film otherwise unobtainable through traditional nanoindentation measurement systems. Technically, the present invention is able to enhance both the accuracy and the capacity of current nanoindentation measurement systems, and facilitates a wider application of the nanoindentation measurement system in terms of industry effect.

DETAILED DESCRIPTION OF THE EMBODIMENTS

With detailed description of the embodiments of the present invention, those skilled in the art will readily appreciate that various modifications and changes can be applied to the embodiments of the invention as hereinbefore described without departing from its scope, defined in and by the appended claims. In addition, the embodiments should not be construed as a limitation on the implementation of applicable description of the invention.

Figure 1:
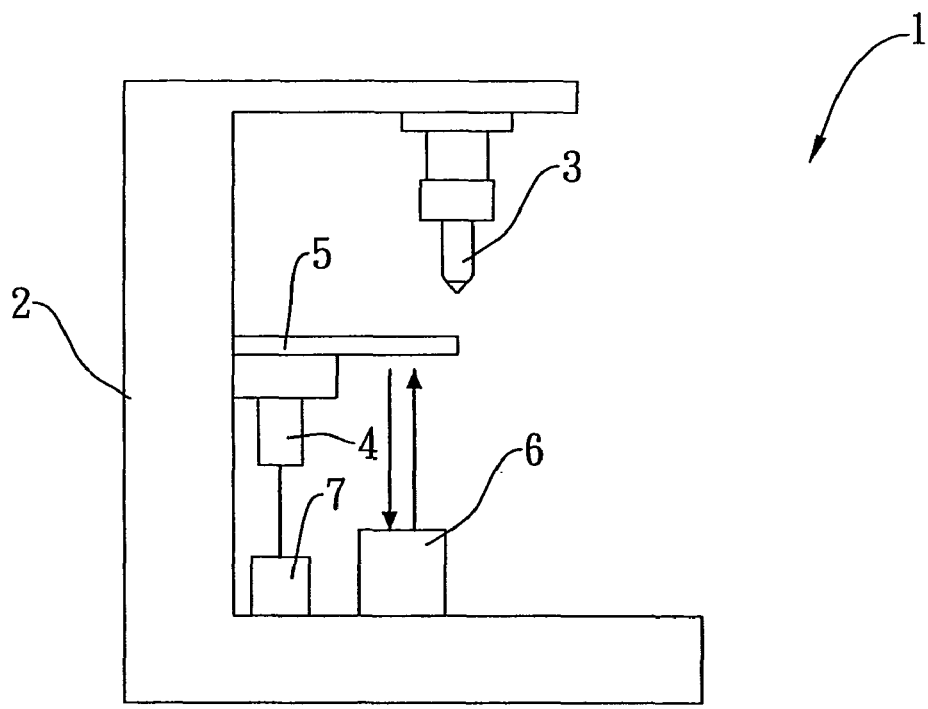
FIG. 1 shows a schematic view of a device for optical nanoindentation measurement according to the present invention.

FIG. 1 shows a schematic view of a device for optical nanoindentation measurement 1 according to the present invention. The device for optical nanoindentation measurement 1 comprises a measuring station 2, an indenter tip 3, a vibrating component 4, thin film 5, and an optical transceiver 6. The indenter tip 3 is mounted on the measuring station 2, capable of moving along the measuring station 2. The vibrating component 4 is mounted on the measuring station 2 for causing the thin film 5 to vibrate. The thin film 5 is placed upon the vibrating component 4, between the indenter tip 3 and the vibrating component 4. The optical transceiver 6 is mounted underneath the thin film 5 for measuring the displacement of the thin film 5.

The device for optical nanoindentation measurement 1 further comprises a function generator 7 connected to the vibrating component 4 for providing vibration signals with different frequencies to the vibrating component 4 to have the vibrations generated by the vibrating component 4 transmitted to the thin film 5. The thin film 5 is square shaped. In addition, the vibrating component 4 is coupled to the thin film 5 through either contact or non-contact means, the vibrating component 4 being used to cause the thin film 5 to vibrate.

Figure 2:
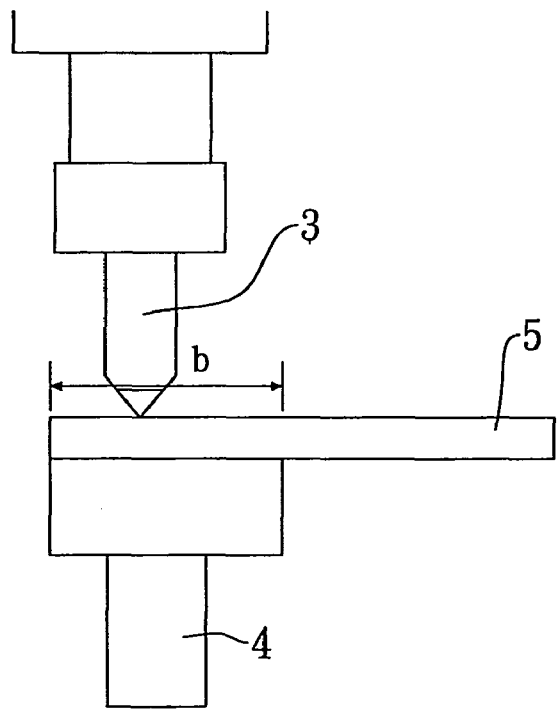
FIG. 2 shows a schematic view of an indenter tip applying load to the fixed portion of thin film.

FIG. 2 shows a schematic view of the indenter tip 3 applying load to a fixed portion of the thin film 5. The thin film takes a geometric form and is connected to the vibrating component. The constituent material of the indenter tip is a specific known material. The measuring device comprises characterizing the mechanical properties of the thin-film. The measuring device comprises a known point of load application.

Figure 5:
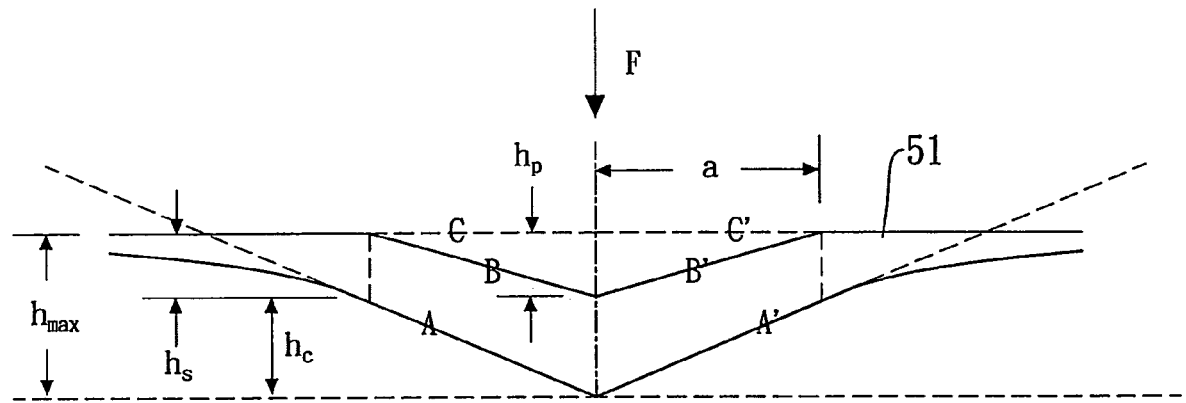
FIG. 5 shows a schematic view of thin film indentation process undertaken by traditional nanoindentation measurement system.

By having the indenter tip 3 make indentation in the fixed portion of the thin film 5 and by applying the formula of $$E_r = \frac{S}{2}\sqrt{\frac{\pi}{A}},$$

a reduced modulus $E_r$ can be obtained, where S stands for the contact stiffness and A stands for the area function of the indentation tip. Both S and A can be obtained by referring to FIG. 5 and FIG. 6. Therefore, by making indentation in somewhere in the fixed portion of the thin film 5, the reduced modulus $E_r$ of the thin film 5 can be obtained by applying the formula of $$E_r = \frac{S}{2}\sqrt{\frac{\pi}{A}}.$$

The Young's modulus $E_2$ and the Poisson's ratio $v_2$ can, further, be obtained according to the relation between $E_r$ and the Young's modulus $E_2$ and the Poisson's ratio $v_2$ of the thin film 5, $$\frac{1}{E_r} = \frac{1-v_1^2}{E_1} + \frac{1-v_2^2}{E_2}.$$

Figure 3:
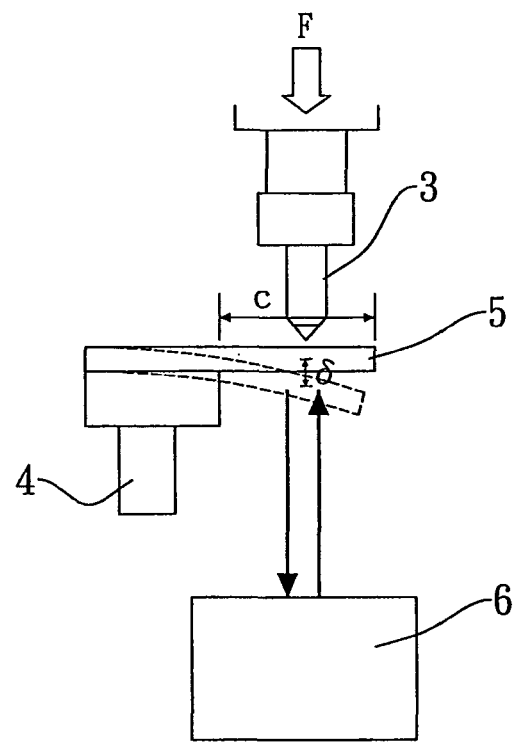
FIG. 3 shows a schematic view of the indenter tip applying load to the non-fixed portion of the thin film.

FIG. 3 shows a schematic view of the indenter tip 3 applying load to a non-fixed portion of the thin film 5, wherein the indenter tip 3 applies a known load F to the non-fixed portion of the thin film 5, causing deflection to the thin film 5. By using the optical transceiver 6 to measure the deflection amount δ of such thin film 5 and by applying the formula of $$F = \frac{3E_2 I}{L^3}\delta,$$

where L stands for the length of the thin film 5 and I represents the moment of inertia of the thin film 5, both are known values, the Young's modulus $E_2$ of the thin film 5 can be obtained.

After the reduced modulus $E_r$ and the Young's modulus $E_2$ of the thin film 5 are obtained, the Poisson's ratio $v_2$ of the thin film 5 can be obtained, too, by applying the formula of $$\frac{1}{E_r} = \frac{1 - v_1^2}{E_1} + \frac{1 - v_2^2}{E_2},$$

where $E_1$ represents the Young's modulus of the indenter tip 3 and $v_1$ represents the Poisson's ratio of the indenter tip 3 with both $E_1$ and $v_1$ being known values.

Figure 4:
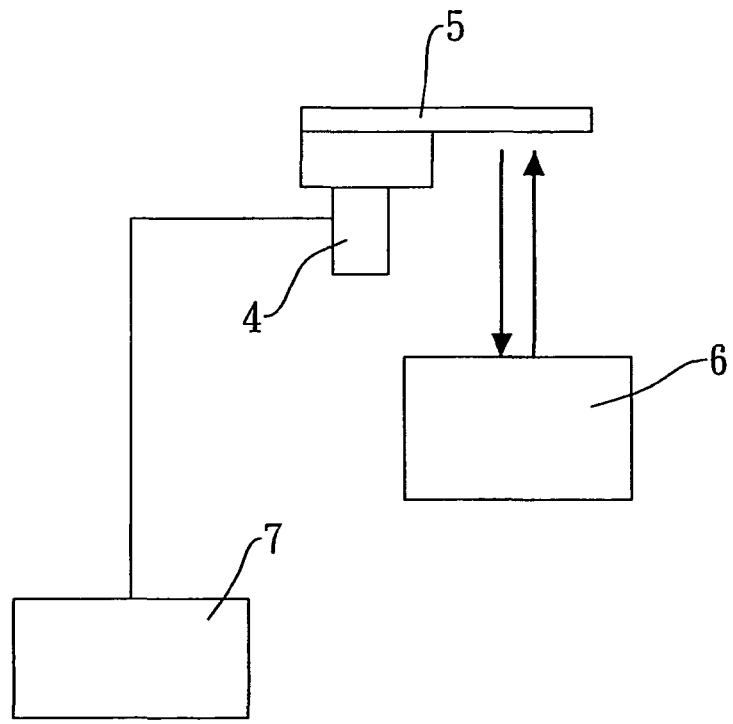
FIG. 4 shows a schematic view of an experiment conducted to obtain the density of the thin film.

FIG. 4 shows a schematic view of an experiment conducted to obtain the density of the thin film 5. According to the invention, the function generator 7, by having the frequency of the function changed, provides frequencies to the thin film 5, by way of the vibrating component 4, to cause the thin film 5 to vibrate. Once the thin film 5 responds to the vibrating component 4 and vibrates, the optical transceiver 6 will be used to measure the mode shape of the vibration of the thin film 5. Through another change of the frequency of the function generator 7, and through another measurement of the mode shape of the vibration of the thin film 5, the $m^{th}$ resonant frequency $f_m$ of the thin film 5 can be obtained. Based on the formula, $$f_m = \frac{(\lambda_m L)^2}{L^2}\sqrt{\frac{E_2 I}{\rho}},$$

derived from the theory of vibration, where $f_m$ is the resonant frequency of the thin film 5, L is the length of the thin film 5, I is the moment of inertia of the thin film 5, $E_2$ is the Young's modulus of the thin film 5, and $\lambda_m L$ is a constant, the density $\rho$ of the thin film 5 can be obtained by applying the respective known values of $f_m$, L, I, $E_2$, and $\lambda_m L$ to the above formula.

A method for optical nanoindentaion measurement applied to a device 1 for optical nanoindentation measurement comprises the following steps of:

having the indenter tip 3 make indentation in a fixed portion of the thin film 5, as shown in FIG. 2 where the fixed portion of the thin film 5 is defined as the area within length b; the reduced modulus $E_r$ being obtained as a result;

having the indenter tip 3 make indentation in a non-fixed portion of the thin film 5, as shown in FIG. 3 where the non-fixed portion of the thin film 5 is defined as the area within length c; the Young's modulus $E_2$ and the Poisson's ratio $v_2$ of the thin film 5 being obtained as a result;

having the optical transceiver 6 measure the displacement amount of the thin film 5; i.e., using the optical transceiver 6 to measure the displacement amount of the thin film 5 after the indenter tip 3 makes indentation in the non-fixed portion of the thin film 5, causing deflection of the thin film 5; the density $\rho$ being obtained as a result;

having the vibrating component 4 provide vibrations with different frequencies to the thin film 5 and having the optical transceiver 6 measure the resonant frequency of the thin film 5; further having the function generator 7 provide vibration signals with different frequencies to the vibrating component 4 to have the vibrations generated by the vibrating component 4 transmitted to the thin film 5.

Through the measurement of the above indentation results, and through the above formula, the Young's modulus, the Poisson's ratio, and the density of the thin film 5 can be obtained.

Figure 6:
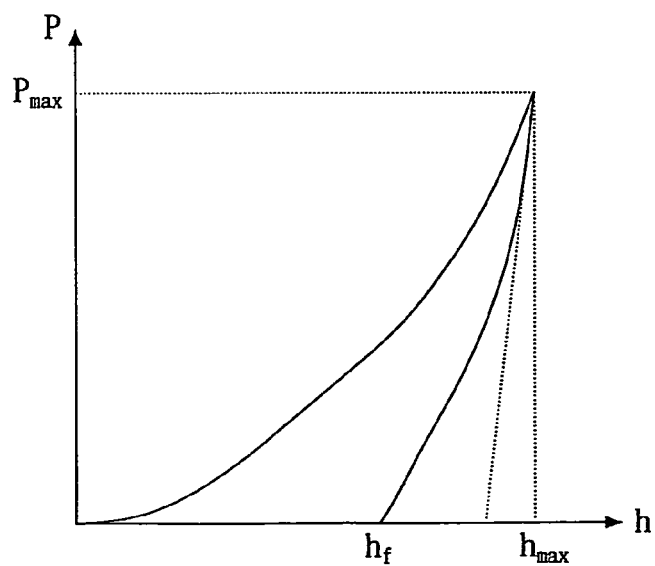
FIG. 6 illustrates the relationship between the applied load and the displacement, as shown in FIG. 5.

The relationship between the contact depth and the projected area of the indenter tip is described as follows. The relationship between the maximum indentation depth $h_{max}$, the contact depth $h_c$, and the distance between the contact position and the initial surface of the thin film 51 is defined as follows: $h_{max} = h_c + h_s$. Besides, according to Oliver and Pharr's findings, the unloading data illustrated in FIG. 6 can be represented by a power-law function: $P = K(h - h_f)^m$, where P is the applied load, $h_f$ is the residual depth, and K and m are constants fitted by the unloading experimental data. The contact stiffness S is defined as the slop of the unloading curve at the time the maximum load is applied, as FIG. 6 shows, and can be obtained through the formula $$S = \frac{dP}{dh}\bigg|_{h=h_{max}}.$$

Moreover, the area function A of the indentation tip of the thin film 51 can be obtained by applying the following formula:

$$A(h_c) = C_0 h_c^2 + C_1 h_c^1 + C_2 h_c^{1/2} + C_3 h_c^{1/4} + \ldots + C_8 h_c^{1/128},$$

where $C_0$ to $C_8$ are fitted constants. And, by applying the theory of contact mechanics, the following relation can be obtained:

$$h_s = \varepsilon \frac{P_{max}}{S},$$

where $\varepsilon$ represents a constant determined by the geometry of the indenter tip. Besides, because $P_{max}$ and S are known, $h_s$ can be obtained as well. In addition, based on the formula $h_{max} = h_c + h_s$, $h_c$ is obtained, and, therefore, the area function $A(h_c)$ is obtained.

The examples given above serve as the embodiments of the present invention only. The examples should not be construed as a limitation on the actual applicable scope of the invention, and as such, all modifications and alterations without departing from the spirits of the invention and appended claims, including other embodiments, shall remain within the protected scope and claims of the invention.

What is claimed is:

1. A device for optical nanoindentation measurement, comprising:

a measuring station;

an indenter tip mounted on the measuring station, capable of moving along the measuring station;

a vibrating component mounted on the measuring station for causing vibration;

a thin film placed upon the vibrating component, between the indenter tip and the vibrating component; and an optical transceiver mounted underneath the thin film for measuring the displacement of the thin film.

2. The device for optical nanoindentation measurement as claimed in claim 1, wherein the vibrating component is used to cause the thin film to vibrate.

3. The device for optical nanoindentation measurement as claimed in claim 1, further comprising a function generator connected to the vibrating component for providing vibration signals with different frequencies to the vibrating component to have the vibrations generated by the vibrating component transmitted to the thin film.

4. The device for optical nanoindentation measurement as claimed in claim 1, wherein the thin film takes a geometric form.

5. The device for optical nanoindentation measurement as claimed in claim 1, wherein the thin film is connected to the vibrating component.

6. The device for optical nanoindentation measurement as claimed in claim 1, wherein the constituent material of the indenter tip is a specific known material.

7. The device for optical nanoindentation measurement as claimed in claim 1, wherein the use of the device comprises characterizing the mechanical properties of the thin film.

8. The device for optical nanoindentation measurement as claimed in claim 1, comprising a known point of load application.

9. A method for optical nanoindentation measurement, comprising the steps of:
   having an indenter tip make indentation in a fixed portion of a thin film;
   having the indenter tip make indentation in a non-fixed portion of the thin film;
   having an optical transceiver measure the displacement amount of the thin film;
   having a vibrating component provide vibrations with different frequencies to the thin film and having the optical transceiver measure the resonant frequency of the thin film; and
   measuring the above indentation results so as to obtain a Young's modulus, a Poisson's ratio, and a density.

10. The method for optical nanoindentation measurement as claimed in claim 9, wherein the non-fixed portion of the thin film is located at a predetermined distance from the fixed portion of the thin film.

11. The method for optical nanoindentation measurement as claimed in claim 9, wherein the displacement of the thin film measured by the optical transceiver represents the deflection of the thin film caused by the indentation made by the indenter tip in the non-fixed portion of the thin film.

12. The method for optical nanoindentation measurement as claimed in claim 9, further comprising a function generator connected to the vibrating component for providing vibrations with different frequencies to the vibrating component.

13. The method for optical nanoindentation measurement as claimed in claim 9, wherein the indentation made by the indenter tip in the fixed portion of the thin film is used to obtain a reduced modulus $E_r$, where $$E_r = \frac{S}{2}\sqrt{\frac{\pi}{A}},$$

and the relation between $E_r$ and the Young's modulus $E_2$ and the Poisson's ratio $v_2$ of the thin film is defined by $$\frac{1}{E_r} = \frac{1-v_1^2}{E_1} + \frac{1-v_2^2}{E_2},$$

where S stands for the contact stiffness, A stands for the area function of the indentation tip, $E_1$ represents the Young's modulus of the indenter tip, $E_2$ represents the Young's modulus of the thin film, $v_1$ represents the Poisson's ratio of the indenter tip, and $v_2$ represents the Poisson's ratio of the thin film.

14. The method for optical nanoindentation measurement as claimed in claim 13, wherein the contact stiffness S is defined by:

$$S = \frac{dP}{dh}\bigg|_{h=h_{max}},$$

where P is the applied load and $h_{max}$ is the maximum load displacement of the indenter tip.

15. The method for optical nanoindentation measurement as claimed in claim 14, wherein the applied load P is defined by: $P=K(h-h_f)^m$, where K and m are constants fitted by the unloading experimental data, and $h_f$ represents a residual depth.

16. The method for optical nanoindentation measurement as claimed in claim 13, wherein the area function is defined as follows:

$$A(h_c)=C_0h_c^2+C_1h_c^1+C_2h_c^{1/2}+C_3h_c^{1/4}+\ldots+C_8h_c^{1/128},$$

where $C_0$ to $C_8$ are constants, and $h_c$ represents a contact depth.

17. The method for optical nanoindentation measurement as claimed in claim 16, wherein $h_c$ is defined by: $h_c=h_{max}-h_s$, where $h_{max}$ represents a maximum load displacement and $h_s$ represents the distance between a contact position and the initial surface of the material.

18. The method for optical nanoindentation measurement as claimed in claim 15, wherein the distance $h_s$ between the contact position and the initial surface of the material is defined by:

$$h_s = \varepsilon\frac{P_{max}}{S},$$

where $P_{max}$ represents a maximum applied load, S represents a contact stiffness, and $\varepsilon$ represents a constant determined by the geometry of the indenter tip.

19. The method for optical nanoindentation measurement as claimed in claim 18, wherein the contact stiffness S is defined by:

$$S = \frac{dP}{dh}\bigg|_{h=h_{max}},$$

where P is the applied load and $h_{max}$ is the maximum load displacement of the indenter tip.

20. The method for optical nanoindentation measurement as claimed in claim 19, wherein the applied load P is defined by: $P=K(h-h_f)^m$, where K and m are constants fitted by the unloading experimental data, and $h_f$ represents a residual depth.

21. The method for optical nanoindentation measurement as claimed in claim 20, wherein the indentation made by the indenter tip in the non-fixed portion of the thin film is used to obtain the Young's modulus of the thin film $E_2$ by applying the formula:

$$F = \frac{3E_2 I}{L^3} \delta,$$

and the Poisson's ratio of the thin film $v_2$ by applying the formula:

$$\frac{1}{E_r} = \frac{1-v_1^2}{E_1} + \frac{1-v_2^2}{E_2},$$

where F represents the load applied by the indenter tip on the non-fixed portion of the thin film, $\delta$ represents the displacement measured by the optical transceiver, L stands for the length of the thin film, and I represents the moment of inertia of the thin film.

22. The method for optical nanoindentation measurement as claimed in claim 21, further comprising the density of the thin film $\rho$ obtainable by applying the formula of $$f_m = \frac{(\lambda_m L)^2}{L^2} \sqrt{\frac{E_2 I}{\rho}},$$

where $f_m$ is the resonant frequency of the thin film, L stands for the length of the thin film, I represents the moment of inertia of the thin film, $E_2$ is the Young's modulus of the thin film, and $\lambda_m L$ is a constant.

* * * * *